(12) United States Patent
Rockman et al.

(10) Patent No.: US 11,596,684 B2
(45) Date of Patent: Mar. 7, 2023

(54) REMOVAL OF AGGLOMERATES

(71) Applicant: Seqirus Pty Ltd, Victoria (AU)

(72) Inventors: Steven Rockman, Victoria (AU); Jesse Bodle, Victoria (AU); Nancy Guzzo-Pernell, Victoria (AU)

(73) Assignee: Seqirus Pty Ltd, Victoria (AU)

( * ) Notice: Subject to any disclaimer, the term of this patent is extended or adjusted under 35 U.S.C. 154(b) by 49 days.

(21) Appl. No.: 17/258,811

(22) PCT Filed: Jul. 10, 2019

(86) PCT No.: PCT/AU2019/050721
§ 371 (c)(1),
(2) Date: Jan. 8, 2021

(87) PCT Pub. No.: WO2020/010394
PCT Pub. Date: Jan. 16, 2020

(65) Prior Publication Data
US 2021/0268100 A1   Sep. 2, 2021

(30) Foreign Application Priority Data

Jul. 10, 2018   (AU) ................................ 2018902497

(51) Int. Cl.
| *A61K 39/145* | (2006.01) |
| *B01J 19/10* | (2006.01) |
| *A61K 39/00* | (2006.01) |

(52) U.S. Cl.
CPC ............. *A61K 39/145* (2013.01); *B01J 19/10* (2013.01); *A61K 2039/5252* (2013.01); *A61K 2039/70* (2013.01); *C12N 2760/16134* (2013.01); *C12N 2760/16234* (2013.01)

(58) Field of Classification Search
CPC .. A61K 2039/70; A61K 39/145; A61K 39/12; A61K 2039/5252; A61K 41/13; B01J 19/10; C12N 13/00; C12N 2760/16234; C12N 2760/16134; G01R 19/14; G01R 31/31917; G01R 31/31928; G01R 19/003; G01R 1/00; G01R 3/00; G01R 5/00; G01R 7/00; G01R 9/00; G01R 11/00; G01R 13/00; G01R 15/00; G01R 19/00; G01R 17/00

See application file for complete search history.

(56) References Cited

U.S. PATENT DOCUMENTS 3,989,818 A    11/1976  Polson
2009/0130131 A1    5/2009  Kido et al.

FOREIGN PATENT DOCUMENTS

| CN | 101024081 A | 8/2007 |
| WO | WO1994019013 | * 1/1994 |
| WO | WO 94/19013 | 9/1994 |
| WO | WO 2007/048086 A2 | 4/2007 |
| WO | WO 2008/040060 A1 | 4/2008 |
| WO | WO 2009/097174 A2 | 8/2009 |
| WO | WO 2009/143524 A2 | 11/2009 |
| WO | WO 2012/055951 A2 | 5/2012 |
| WO | WO 2012/090002 A1 | 7/2012 |
| WO | WO 2013/057719 A2 | 4/2013 |
| WO | WO 2015/082905 A1 | 6/2015 |

OTHER PUBLICATIONS

International Search Report for PCT/AU2019/050721, dated Aug. 20, 2019, 8 pages.
Written Opinion of the International Search Authority for PCT/AU2019/050721, dated Aug. 20, 2019, 6 pages.

* cited by examiner

*Primary Examiner* — Bao Q Li
(74) *Attorney, Agent, or Firm* — Finnegan, Henderson, Farabow, Garrett & Dunner, LLP

(57) ABSTRACT

The present disclosure provides a method of dispersing agglomerated material in a preparation comprising influenza proteins. The method comprises subjecting the preparation to sonication.

20 Claims, 11 Drawing Sheets

REMOVAL OF AGGLOMERATES

CROSS REFERENCE TO RELATED APPLICATIONS

The present application is a national stage entry of PCT/AU2019/050721, filed Jul. 10, 2019, which claims priority from Australian Application No. 2018902497 filed on Jul. 10, 2018 and entitled "Removal of agglomerates". The entire contents of each application are hereby incorporated by reference.

FIELD

The present disclosure relates to a method of dispersing agglomerates in a preparation comprising influenza antigens and in particular, the use of this method in the production of influenza vaccines.

BACKGROUND

Influenza vaccines are considered the most effective method to prevent infection. The first influenza vaccines were whole virus preparations [1]. The current manufacturing process of inactivated trivalent and quadravalent influenza vaccines (TIV and QIV respectively) is based upon chemical disruption or "splitting" of the influenza virus, which was introduced in the 1960s [2]. Chemical disruption (by detergent or solvent) was found to reduce the reactogenicity of the vaccine without, in many cases, compromising the immunogenicity. Due to the high volatility of solvents, all commercially available influenza vaccines are disrupted or split with detergent. However, the concentration of detergent utilized to disrupt the whole virion exceeds acceptable limits within the vaccine and therefore must be removed to permissible levels.

The consequence of removal of the detergent is that the resulting split virions develop agglomerates or agglomerated material. The development of agglomerates relates to the strain and the level/type of detergent utilized in the splitting process. In many cases vaccines and other pharmaceutical products contain either residual detergent or an additional detergent/chemical to maintain appropriate quality attributes of the vaccine. However, it has long been established that the presence of detergent, in particular in the context of vaccination, renders antigens more soluble potentiating a decrease in the immunogenicity and hence effectiveness of the vaccine.

SUMMARY

The present disclosure provides a method of dispersing agglomerated material in a preparation comprising influenza proteins or virus, the method comprising subjecting the preparation to sonication.

The present disclosure also provides a method of producing an influenza vaccine the method comprising producing a preparation comprising inactivated or split influenza virions and sonicating the preparation.

DETAILED DESCRIPTION

The present disclosure describes the use of a sonication method to effectively disperse agglomerated material in influenza virus vaccine (IVV) drug substance or IVV drug product and will be referred to here after as IVV Drug Matrix. The feasibility of sonication was assessed on the H3N2 strain of influenza virus since this sub-strain of influenza A exhibits the greatest level of agglomeration compared to non-H3N2 strains and B influenza.

One example of the disclosure provides a previously unseen approach since inhibition of protein agglomeration is commonly achieved by the addition of a compatible excipient(s) to the formulation. For example, excipients such as sugars, polyols, amino acids, salts, polymers and surfactants have been found to stabilize agglomerates by preferential interactions [(Arakawa et al (1991); Timasheff (1998)], increased rate of protein folding [Wang et al (1995); Frye and Royer (1997)], reduction of solvent accessibility and conformational mobility [Kendrick et al (1997)] as well as increased solvent viscosities [Jacob and Schmid (1999)].

The present disclosure avoids the need for these additives, which can adversely impact the immunogenicity of the vaccine and cause unwanted side effects in individuals receiving the vaccine.

In one example, the disclosure provides a method of dispersing agglomerated material in a preparation comprising influenza proteins, the method comprising subjecting the preparation to sonication.

In another example, the disclosure provides a method of producing an influenza vaccine the method comprising producing a preparation comprising inactivated or split influenza virions and sonicating the preparation.

Preparation for sonication can be whole virion, split virion, subunit vaccine or recombinant vaccine. In order to facilitate filtration for sterility of the preparation it is preferable that the percentage of agglomerates is less than 10% in the final preparation.

In an example, the preparation comprises influenza haemagluttinin, for example, the preparation comprises split influenza virions. In one example, the preparation is substantially free of detergent. As used herein, the phrase "substantially free of detergent" means having a level of less than 0.02%. For example, the level of detergent is less than 200 ppm. In a further example, the level of detergent is less than 50 ppm.

Typically the sonication is conducted for a time and at intensity such that at least 50% of agglomerates present in the preparation are dispersed. The sonication energy produced for the disruption of agglomerates can be delivered to the target IVV Drug Matrix by one of three ways: (1) Energy is transferred directly via the Sonicator probe suspended in the IVV Drug Matrix, (2) IVV Drug Matrix passes across the vibrating tip of the sonicator's probe tip enclosed in a flow-through device or (3) Indirect energy transfer through metal or glass tubing to where the IVV Drug Matrix passes through. All sonication methods require the transfer of at least 89 Joules/mL of energy to disperse at least 50% of the agglomerates within the IVV Drug Matrix.

The vaccine produced by the method of the present disclosure may be a monovalent seasonal vaccine or a monovalent pandemic vaccine. In another example, the vaccine of the present disclosure is a multivalent vaccine such as trivalent and quadravalent vaccines.

The vaccine produced by the method of the present disclosure typically comprises influenza A and influenza B antigens and is, for example, substantially free of agglomerated material. In one example, the phrase "substantially free of agglomerated material" means that more than 50% (about 90 Joules/mL sonication) of the material is not aggregated. In a further example, at least 60% (about 134 Joules/mL sonication), 70% (about 178 Joules/mL sonication) or 80% (about 223 Joules/mL sonication) of the material is not aggregated. In another example, at least 90% (about 267 Joules/mL sonication) of the material is not aggregated.

As is described below the method of the present disclosure provides a number of unexpected advantages. Firstly, the method is highly efficient at dispersing agglomerates present in the influenza antigen preparation. Surprisingly these dispersed agglomerates do not re-aggregate despite extended periods of storage (4° C.). Further it was shown that a vaccine produced using the method of the present disclosure was able to elicit a stronger immune response in the ferret model than vaccines comprising the same antigens but untreated or treated with additives to disperse agglomerates.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavor to which this specification relates.

All publications mentioned in this specification are herein incorporated by reference in their entirety.

It must be noted that, as used in the present specification, the singular forms "a", "an" and "the" include plural forms unless the context clearly dictates otherwise. Thus, for example, reference to "an agent" includes a single agent, as well as two or more agents; reference to "a molecule" includes a single molecule, as well as two or more molecules; and so forth.

Examples

Methods

Sonication of IVV Drug Matrix

Direct Probe Sonication Method

IVV Drug Matrix was processed using a 'direct' sonication method, whereby the sonicator horn/probe is immersed directly into the sample contained within a beaker.

A Branson Model 450 Sonifier® (Branson Ultrasonics) was used to perform sonication and comprised four components, including a power unit, model 102C convertor and a 0.5 inch tapped horn.

To assess the efficiency of the sonication process, a Bandelin SONOPULS Sonicator (Bandelin Electronic GmbH & Co. KG) was used. The setup consisted of a GM3200 Sonifier power unit, UW3200 convertor, SH213G booster and TT13 13 mm titanium tip. Sonication of IVV drug substance material was performed in a beaker as per the method described for the Branson Sonicator.

IVV Drug Matrix samples were prepared in 10 ml batches and placed in a clean 30 ml beaker, which was secured onto a clamp stand with the Sonicator probe sufficiently immersed into the sample solution (i.e. the distance between the Sonicator tip and the base of the beaker was approximately 1 mm). Sonication was then performed delivering a range of energy input while varying the rate of energy transfer (amplitude):

The range of sonication energy delivered was measured as Joules (energy) per milliliter of IVV Drug Matrix and included: 0 Joules/mL, 83 Joules/mL, 165 Joules/mL, 259 Joules/mL, 345 Joules/mL.

To avoid overheating of the sample, sonication was conducted in at least two parts and the beaker left to cool briefly on ice in between processing. Final sonicated IVV drug substance samples were transferred into plastic tubes and stored at 2-8° C. prior to further analysis.

Flow-Through Sonication Method

To assess the scalability of the sonication process, a Bandelin SONOPULS Sonicator (Bandelin Electronic GmbH & Co. KG) fitted with a flow-through device was used. The setup consisted of a GM3200 Sonifier power unit, UW3200 convertor, SH213G booster, TT13 13 mm titanium tip and a DG 4 G flow through processing vessel. Sonication of IVV drug substance material was circulated through the sonicator's flow-through device by means of a 520U peristaltic pump (Watson & Marlow, Australia).

Measurement of Agglomerated Material
Optical Density Turbidity (ODT) Assay

Figure 3:
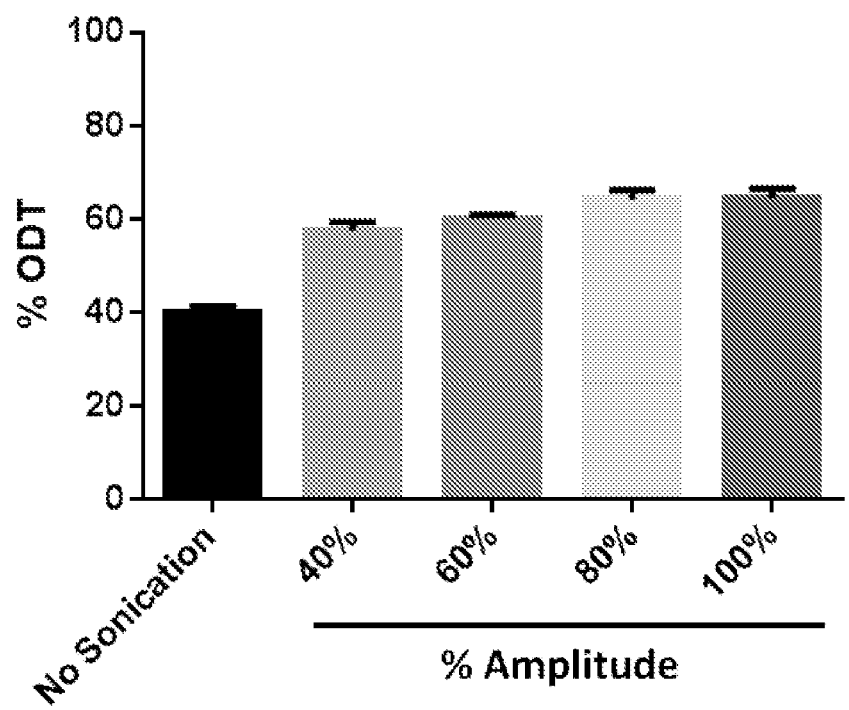
FIG. 3: Influence of sonication with respect to intensity of energy input (amplitude) on dispersion of H3N2 A/Victoria/361/2011 IVV Drug Matrix, by ODT analysis.

To assess the degree of non-agglomerated material in the vaccine intermediate product IVV drug substance, the level of recovered protein utilizing optical density (OD) at A280 nm of the supernatant following the application of a modest centrifugal force was determined (Tay et al: Investigation into alternate testing methodologies for characterization of influenza vaccine. Human Vaccine Immunotherapy 2015 11 (7) 1673-84). Since the proportion of protein in the pellet after centrifugation directly correlates to the degree of agglomerated material within the sample, a higher recovery in the supernatant would correspond to a greater proportion of dispersed protein. This assay was termed the optical density turbidity (ODT) method; protein recovery values range from 0 to 100% (presented as % ODT herein), which increase with the amount of dispersed protein in the sample.

Several attributes of the assay were evaluated for three influenza strains, including H1N1; A/California/07/2009, H3N2; A/Victoria/361/2011 and B; B/Hubei Wujiagang/158/158/2009. Validation results demonstrated repeatability (% CV) of 2.9, 3.1 and 3.1% (respectively), precision inter-lot variability (% CV) of 8.8, 6.5 and 3.4% (respectively), intermediate precision of 0.4%, 6.3% and 0.2% (respectively), statistically insignificant differences between operators of p=0.81, 0.13 and 0.78, (respectively), and expectable linearity between expected and observed results (R=0.9685). Typical % ODT profiles for replicate lots of IVV drug substance representing seasonal vaccine subtypes: H1N1, H3N2 and Influenza B are detailed in FIG. 1.

Further this assay was correlated with alternative methods of agglomeration characterization, including dynamic light scattering (DLS) and asymmetric field flow fractionation (A4F). The low level of variation from ODT analysis indicated that this assay was highly suitable for the assessment of agglomeration in intermediate vaccine material.

Dynamic Light Scattering (DLS)

Particle size analysis by DLS was used as a complementary method to the ODT assay to further understand the agglomeration characteristics within the samples. The DLS technique is based on the measurement of the Brownian motion of proteins in solution, which is the random movement of particles due to collisions with the surrounding solvent molecules. The Brownian motion induces time dependent fluctuations in the intensity of scattered light which is measured by DLS and generates a particle size distribution (PSD) for the sample.

DLS measurements were performed using the Malvern Zetasizer Nano Series ZS (Malvern Instruments Ltd). Several properties which influence the Brownian motion of particles in solution was pre-determined, including the density (DA-100M Density Meter, Mettler Toledo), viscosity (Lovis 2000M Microviscometer, Anton Paar) and refractive index (30GS Refractometer, Mettler Toledo) of each sample analyzed. Pre-treatment of samples involved centrifugation for 1 minute at 8000 rpm to remove any extraneous material or sediment containing large particles which are unstable and subsequently interfere with the analysis. The resulting supernatant component of each sample was then withdrawn and assessed by DLS; each sample measurement was based on five replicates (n=5) performed at a backscatter angle of 173° and equilibrated to a temperature of 25° C. for three minutes.

Influenza Antigenicity Assessment

Single Radial Immunodiffusion (SRID)

SRID assays were performed as previously described [Williams et al, 1980]. Briefly, reference and test antigen material was diluted 1:1, 2:3 and 1:3 in PBS-containing 1% Zwittergent solution (Calbiochem, Darmstadt, Germany), and added to duplicate wells of agarose gels containing polyclonal antiserum. Gels were incubated for 72 hrs in humidified chambers, dried onto glass plates, and stained with Coomassie brilliant blue R-250 (Sigma, Calif., USA). Circular zones of antigen-antibody precipitation were measured, and HA concentration was calculated by the parallel line bioassay method in comparison to IZP standards (15), and test validity was confirmed using a 'g' test (g≤0.061) (16).

Electron Microscopy (EM) Imaging

Negative staining EM was performed by the agar diffusion filtration method adopted by Hayat and Miller (1990). Three grids of each sample were prepared; IVV drug substance was diluted 1 in 50 with phosphate buffered saline (PBS; pH 7.2) to provide a discontinuous monolayer. The sample (1 μL) was applied to a formvar-coated copper electron microscope grid, which was then inverted onto a 2% w/v agar plate. Upon settling of the grids onto the agar plate (i.e. the liquid absorbed by the agar), the grid was floated on a drop of negative stain (2% w/v sodium phosphotungstate at pH 7.0). After twenty seconds, the grid was then lifted and excess stain removed by contacting the edge of the grid with a small strip of torn Whatman No. 1 filter paper. The remaining thin film of stain was left to air-dry prior to examination by the electron microscope.

Results

Disruption of Agglomerated IVV Drug Matrix by Sonication

The most effective method to disperse agglomerated material was determined using a H3N2 sub-strain of influenza because of its propensity to form the greatest level of agglomerated material post-detergent disruption. Several methods were assessed to establish whether agglomerated material following detergent disruption could be dispersed.

The first approach involved using high frequency sound waves by sonication to disperse agglomerates within IVV drug substance material of A/Victoria/361/2011, sub-type H3N2 (FIG. 2). A direct sonication method was used in which localized and highly intense ultrasonic waves of energy could be transmitted directly from the probe and into a beaker containing the sample. The samples (prepared in 10 ml batches) were subjected to a range of sonication input energy ranging from 83 Joules/mL-345 Joules/mL and the extent of dispersion evaluated by the ODT assay. The results demonstrate a linear relationship between the amount of energy input and the level of agglomerates disassociated, i.e. % ODT values ranged from 50% to 80% after sonication compared with 40% when untreated (FIG. 2). Interesting to note was that the level of dispersion reached a maximum at 259 Joules/mL, from which no further increase in dispersion was observed. In contrast, mild heating and stirring of the IVV drug substance (30 mins at 37° C. with stirring 600 rpm) did not alter the level of dispersed material.

The intensity at which energy was transferred into IVV drug substance was explored by adjusting the sonication amplitude (0-100%) while the exposure time remained constant at 0.70 s/ml for all samples. ODT results indicated a predictable trend as previously seen with respect to the amount of energy transferred, where the extent of dispersion in IVV drug substance increased with sonication amplitude when exposure time was kept consistent (FIG. 3). An optimal rate of sonication energy transfer was achieved at 80% amplitude, beyond which there is no further elevation in the level of agglomerate dissociation. These results suggest 80% is an optimal amplitude (i.e. rate of energy transfer) for dissociating agglomerates.

Feasibility of Sonication for Dispersing IVV Drug Matrix Material

To be acceptable inactivated vaccines require consistent quality attributes. That is, if a method has been shown to disperse agglomerated material it is important that the material retains this characteristic.

A study was conducted over 24 weeks to assess the feasibility of sonication as a method to disperse agglomerated material in IVV Drug Matrix of H3N2 A/Victoria/210/2009, both in the presence and absence of a detergent, Polysorbate 80 (PS80). To monitor various characteristics of the samples a multitude of tests were employed, including ODT and DLS for agglomeration assessment, single radial immunodiffusion (SRID) for antigenicity and electron microscopy (EM) for morphological imaging.

Agglomeration Behavior by ODT and DLS

Figure 4:
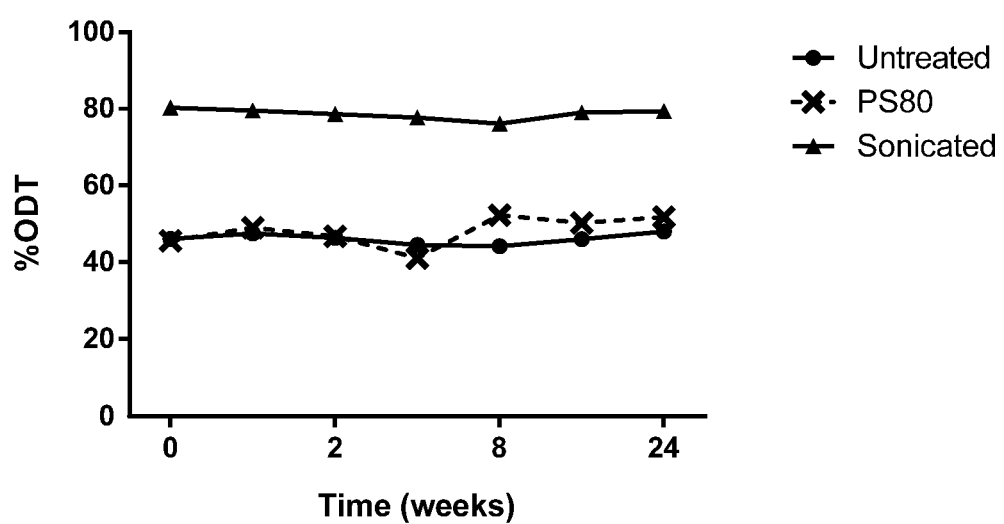
FIG. 4: ODT results demonstrating sonication effectively disperses agglomerates and maintains the dispersed state of H3N2 A/Victoria/210/2009 IVV Drug Matrix over time, compared with untreated and PS80-treated samples.

The agglomeration characteristics of the untreated, sonicated and PS80-treated IVV Drug Matrix were evaluated by the ODT assay and DLS. ODT analysis demonstrated that following sonication (at least 200 Joules/mL), the level of dispersed material in IVV Drug Matrix reached 80% compared to 40% for the non-sonicated material (at time 0) (FIG. 4). This level of dispersion remained consistent over 24 weeks at 4° C. indicating an irreversibly dispersed state (FIG. 4). Further there was no increase in dispersion or further agglomeration of the control (untreated) material over this time. The addition of a detergent (0.1% PS80) had no notable impact upon the level of agglomerates in this material compared to the initial level. Hence, this indicated the level of agglomeration of IVV Drug Matrix material is set following disruption of detergent.

Figure 5:
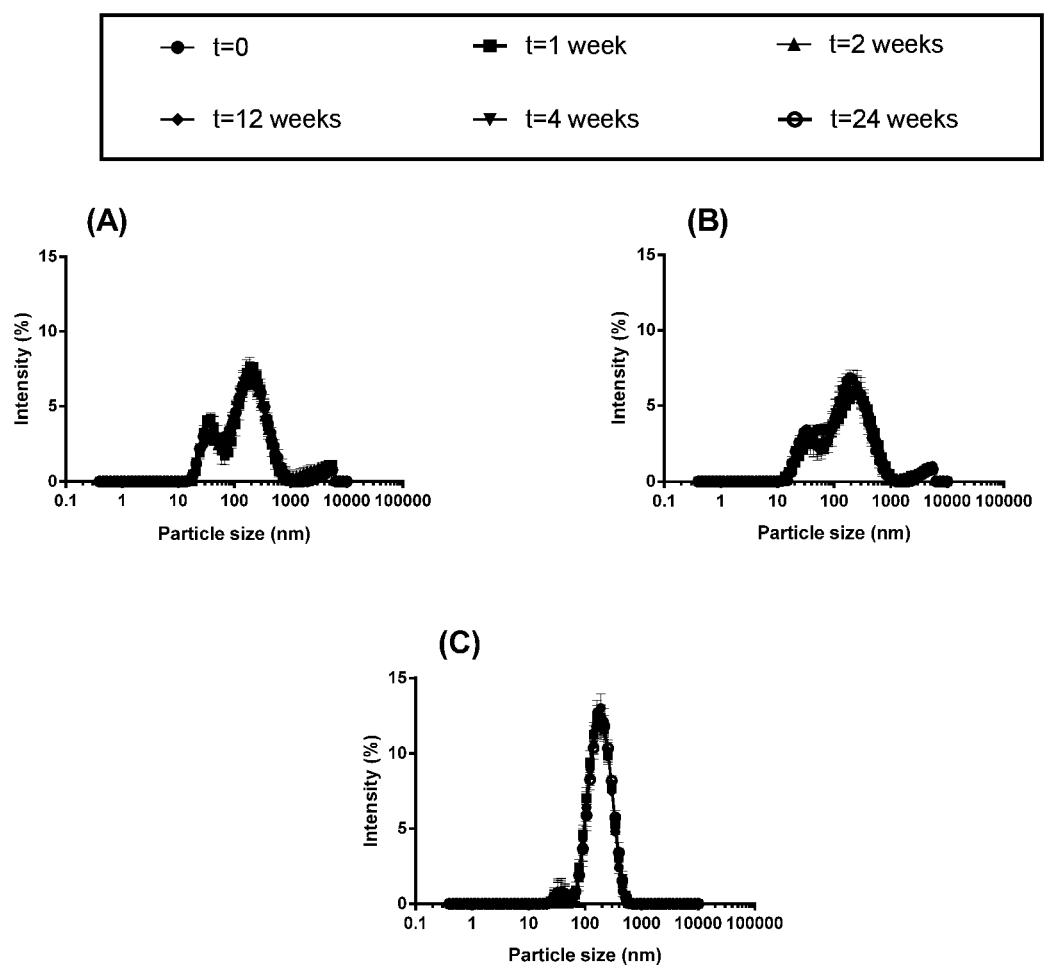
FIG. 5: Average intensity particles size distribution (PSDs) (n=5) of (A) untreated, (B) PS80-treated and (C) sonicated H3N2 IVV Drug Matrix of A/Victoria/210/2009, analyzed by DLS over 24 weeks.

In conjunction with the ODT assay, samples were analyzed by DLS to further characterize agglomeration. For each sample, DLS measurements (n=5) generated an intensity particle size distribution (PSD), which demonstrates the relative intensity of light scattered by particles in various size populations. Results for DLS revealed a close correlation with those of ODT for all three samples (FIG. 5). For example, the untreated and PS80-treated IVV Drug Matrix samples demonstrated multimodal PSDs with peaks present at 60, 400 and 7000 nm thus indicating agglomerates within (FIGS. 5A and B). However, sonication treatment produced a mono-modal distribution with a single distinct peak present at 300 nm, suggesting a uniform and well dispersed sample that was devoid of agglomerates (FIG. 5C). At each time point of analysis, all samples generated reproducible PSDs and further remained unchanged over the course of the 24 week period.

Antigenicity by SRID and EIA

Figure 6:
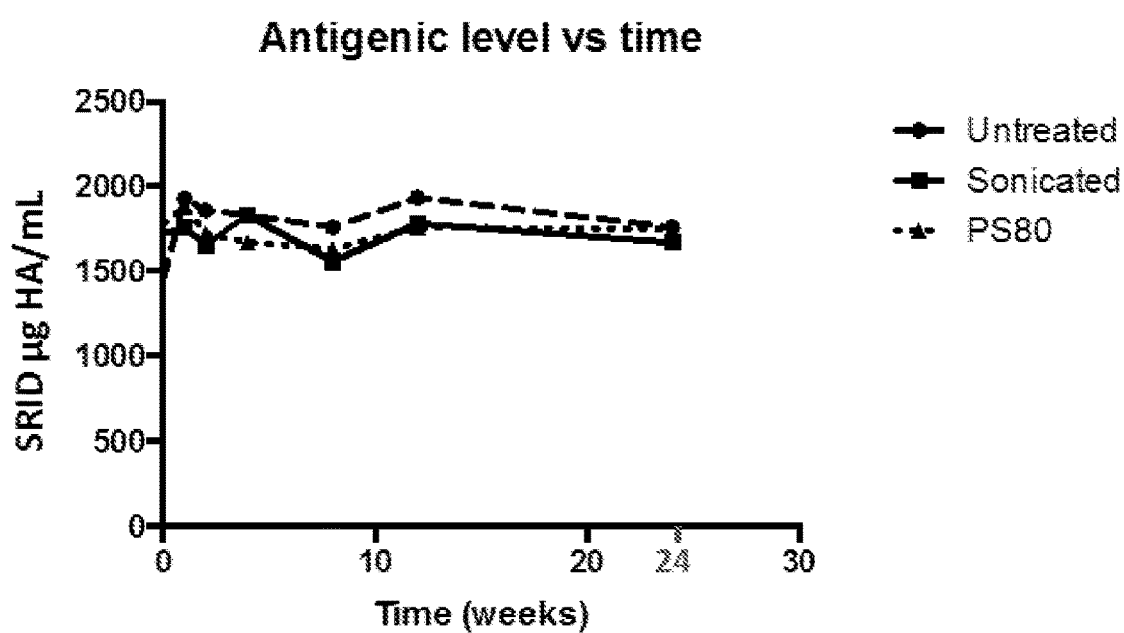
FIG. 6: Single radial immunodiffusion (SRID) analysis of untreated, detergent (PS80)-treated and sonicated IVV Drug Matrix (H3N2; A/Victoria/210/2009) over 24 weeks.

The level of antigenic material was assessed by SRID to determine whether sonication or the addition of detergent affected the influenza antigen. SRID analysis indicated that regardless of whether the material was sonicated or treated in the presence of a detergent, the level of antigenic material remained at the same potency as that of the untreated sample and was constant over time (Table 1, FIG. 6).

TABLE 1

SRID results of untreated, detergent (PS80)-treated and sonicated IVV Drug Matrix (H3N2; A/Victoria/210/2009) over time.

| | Potency (µg HA/mL) | | | | | |
|---|---|---|---|---|---|---|
| Weeks | 0 | 2 | 4 | 8 | 12 | 24 |
| Untreated | 1451.5 | 1860.0 | 1829.2 | 1760.3 | 1934.4 | 1759.3 |
| Sonicated | 1722.5 | 1657.5 | 1829.2 | 1559.1 | 1779.8 | 1670.8 |
| PS80 | 1740.0 | 1710.6 | 1654.5 | 1578.8 | 1780.7 | 1749.8 |

Morphological Imaging by EM

Figure 7:
FIG. 7: EM micrographs representing IVV Drug Matrix (MPH), IVV Drug Matrix post sonication (Sonicated MPH) and IVV Drug Matrix in the presence of polysorbate 80 (MPH+PS80). All samples were analyzed by EM at 0, 1, 2 and 6 month time points.

Imaging by EM was used to examine the morphological appearance of the samples at 0, 1, 2 and 6 month time-points (FIG. 7). Notable differences were observed between sonicated and control IVV Drug Matrix samples. Control/untreated IVV Drug Matrix (with and without PS80) contained significant amounts of agglomerates throughout the entire 6 month time course, as represented by the darker regions in the micrographs. In contrast, sonicated IVV Drug Matrix contained fewer agglomerates that were reduced in size and the appearance of the material remained consistent for the period of time examined. These observations reflected the results obtained from both ODT and DLS analyses, in which sonicated material was evidently more dispersed than IVV Drug Matrix that was untreated or incorporated a detergent (PS80).

Applicability of Sonication to all Seasonal Strains of Influenza

Figure 1:
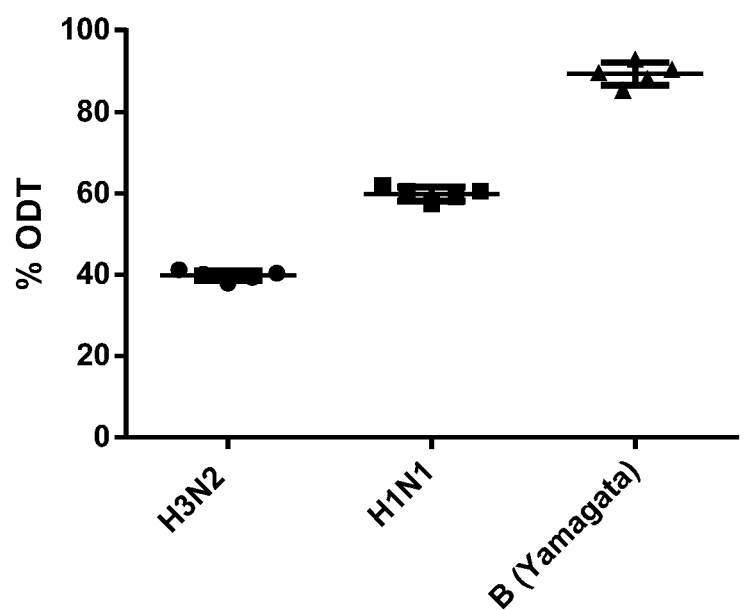
FIG. 1: Repeatability of optical density turbidity (ODT) assay for influenza virus vaccine (IVV) IVV Drug Matrix of strains of A/Victoria/361/2011 (H3N2), A/California/07/2009 (H1N1) and B/Hubei-Wujiagang/158/158/2009 (B Yamagata).
Figure 2:
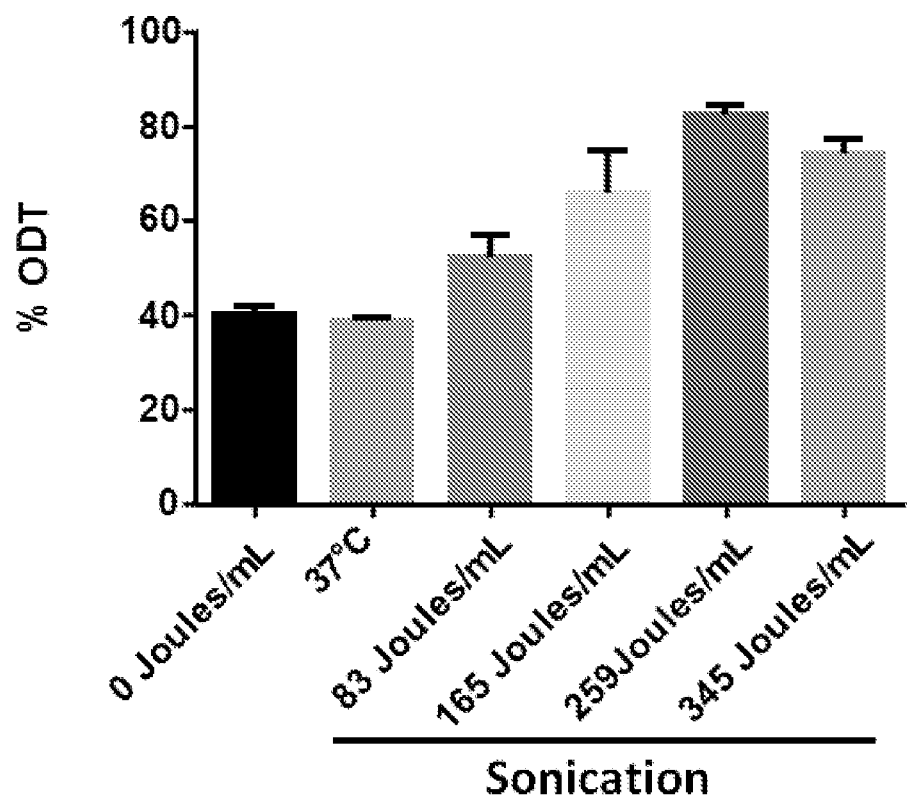
FIG. 2: Influence of sonication with respect to the amount of energy delivered (Joules/mL) and heat (37° C., 30 min) on dispersion of H3N2 A/Victoria/361/2011 IVV Drug Matrix, by ODT analysis.
Figure 8:
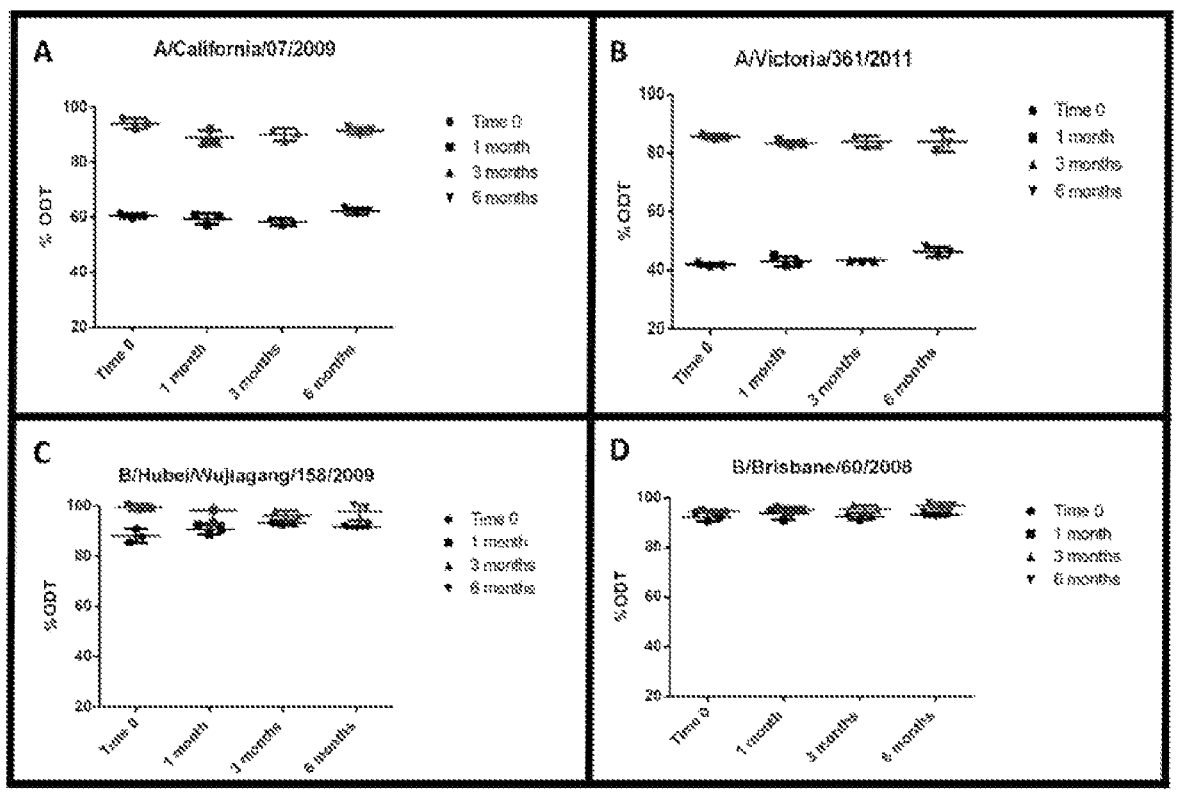
FIG. 8: ODT results for four seasonal strains (A/Victoria/361/2011 (H3N2), A/California/7/2009 (H1N1), B/Hubei-Wujiagang/158/2009 (B Yamagata) and B/Brisbane/60/2008 (B Victoria)) of influenza, pre- and post-sonication treatment (Son) at time 0, 3 and 6 months.

While H3N2 displays the greatest level of agglomeration (FIG. 1) compared to other seasonal strains, it is essential to demonstrate that this method is able to disrupt agglomerates of all strains. Four seasonal strains were examined for the level of agglomerates dispersed, pre- and post-sonication (at least 200 Joules/mL), over a period of six months (FIG. 8). In all virus preparations examined, the application of sonication increased the level of dispersed material and this material remained dispersed over a six month period. The elevation in agglomerate dispersion upon sonication treatment appeared more pronounced for the two sub-strains of influenza A, H3N2 and H1N1, in comparison with the two influenza B viruses derived from the Yamagata and Victoria lineages. For example, the level of dispersed material increased by approximately 60-100% for the two A strains compared with a 3-10% increase for the B strains.

Figure 9:
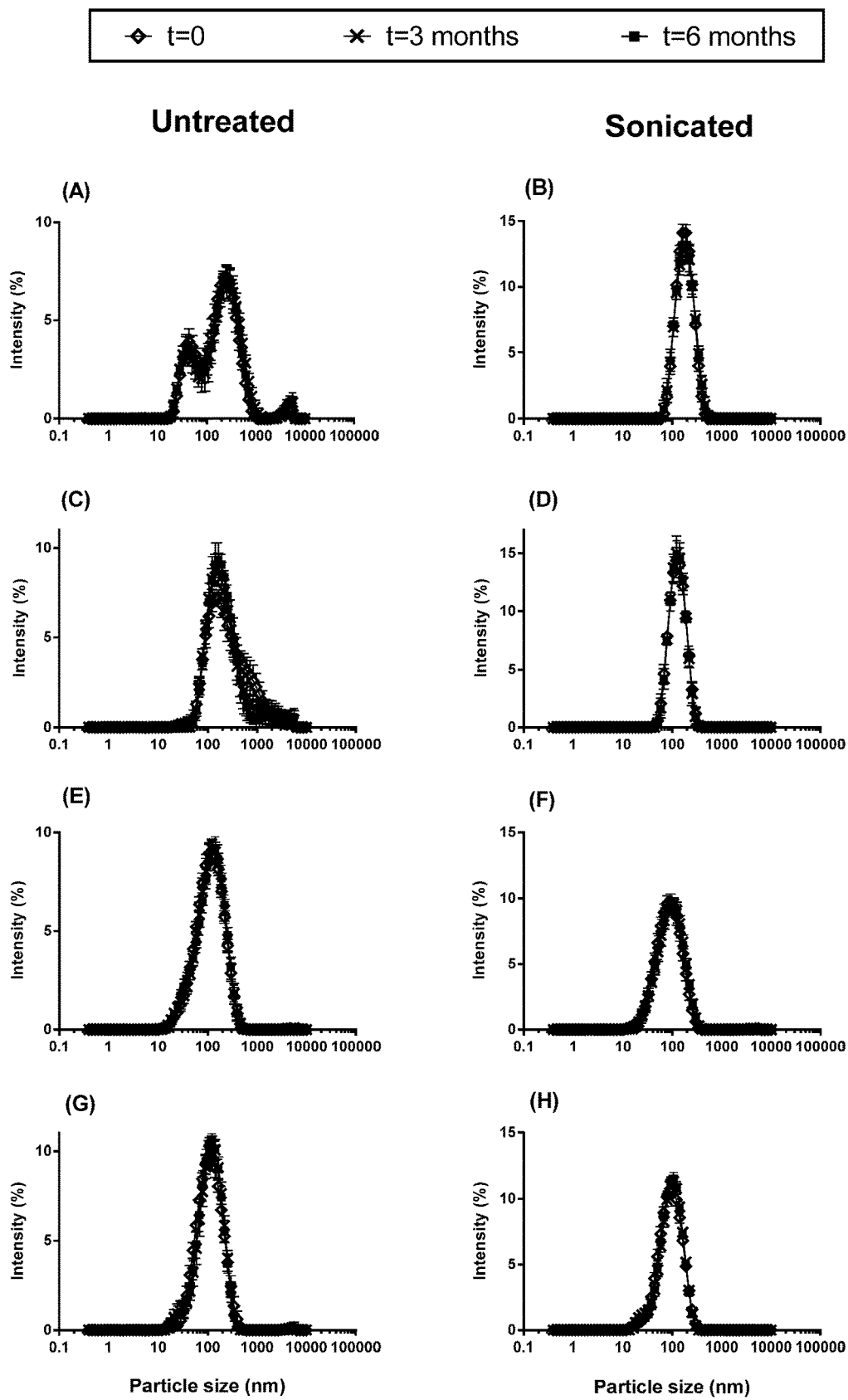
FIG. 9: Average particle size distributions (PSDs) (n=5) of untreated (left) and sonicated (right) IVV Drug Matrix material for A/Victoria/361/2011 (A, B), A/California/7/2009 (C, D), B/Hubei-Wujiagang/158/2009 (E, F) and B/Brisbane/60/2008 (G, H), analyzed by DLS over six months.

The ODT results were further corroborated by the data obtained from DLS analysis of all four influenza strains. Intensity PSDs derived from five replicate measurements for each sample at 0, 3 and 6 months are shown in FIG. 8. The untreated sample of A/Victoria/361/2011 depicted the presence of agglomerates of various size populations due its multimodal profile (FIG. 9A), whereas the PSDs for A/California/7/2009, B/Hubei-Wujiagang/158/2009 and B/Brisbane/60/2008 had more monomodal structure, hence suggesting a more uniform population of particles (FIG. 9 C, E, G respectively). Post sonication, all four strains exhibited distributions that were characteristic of well dispersed IVV Drug Matrix which did not contain any agglomerates (FIG. 9 B, D, F, H).

Stability and Batch Consistency of Sonicated IVV Drug Matrix

IVV Drug Matrix representing 4 vaccine candidate types/subtypes were sonicated to determine both consistency and stability of applying a controlled level of energy (Joules/mL) to achieve a target level of agglomerate dispersion (Table 2, FIG. 8). IVV drug substance for each representative strain was divided into 6 sub aliquots. Three of the 6 aliquots were independently exposed to at least 200 Joules/mL of sonication and stored for up to 6 months at 2-8° C. along with their un-sonicated control groups. Samples were taken from all groups at 0, 1, 3 and 6 months and analysed by ODT for the level of agglomerates present. A significant change in the level of dispersed agglomerates was observed in sonicated samples when compared to un-sonicated controls for all sub-lots within the Influenza A strain subtypes: A/California/07/2009 and A/Victoria/361/2011. There was great consistency amongst sub-lots sonicated independently for both representative Influenza A strains. At time 0 all three sub-lots of the H1N1 and H3N2 strains met the target % ODT (>80%) after sonication, with % CVs of 2.1% and 1.1% respectively, well within the 10% limit. Less of a change in the level of agglomerate dispersion was observed in lots representing B strains due to the low content of agglomerates existing in control groups. Post sonication the B strain sub-lots displayed the same level of batch to batch consistency as lots representing the A strains with % CVs for the B/Hubei Wujiagang/158/2009 and B/Brisbane/60/2008 at time 0 of 1.2% and 0.7% respectively. Importantly sub-lots representing all 4 seasonal influenza strains maintained their elevated level of % ODT and batch to batch consistency for the entire 6 month time-course, suggesting agglomerate disruption by sonication is permanent.

TABLE 2

Batches (n = 3) of IVV Drug Matrix representing 4 seasonal influenza strains pre and post sonication over a 6 month time course : A/California/07/2009, A/Victoria/361/2011, B/Hubei Wujiagang/15 8/2009 and B/Brisbane/60/2008.

| | Pre or Post Sonication | Months | | | |
|---|---|---|---|---|---|
| | | 0 | 1 | 3 | 6 |
| A/California/07/09 (H1N1) | Pre %ODT | 60.4 | 59.4 | 58.2 | 62.2 |
| | Post %ODT | 95.7 | 90.7 | 91.8 | 93.1 |
| | Post %CV | 2.1% | 3.0% | 2.3% | 1.5% |
| A/Victoria/361/11 (H3N2) | Pre %ODT | 41.9 | 43 | 43.4 | 46.2 |
| | Post %ODT | 86.7 | 84.2 | 84.6 | 84.7 |
| | Post %CV | 1.1% | 1.2% | 2.9% | 5.1% |
| B/Hubei Wujiagang/158/09 (B YAM) | Pre %ODT | 88.1 | 90.6 | 93.3 | 91.7 |
| | Post %ODT | 98.6 | 97.3 | 95.4 | 96.9 |
| | Post %CV | 1.2% | 5.0% | 1.9% | 3.8% |
| B/Brisbane/60/08 (B YAM) | Pre %ODT | 92.2 | 93.5 | 92.5 | 93.3 |
| | Post %ODT | 95.4 | 96 | 96.5 | 98.3 |
| | Post %CV | 0.7% | 1.7% | 2.0% | 1.6% |

Linear Relationship for the Number of Predicted Glycosylation Sites on HA and the Amount of Sonication Required.

The enveloped glycoprotein; hemagglutinin (HA) is the sialic acid receptor-binding protein of the influenza virus which enables it to dock with host cells and escape from digestion once engulfed into an endosome. The globular head region of the HA molecule contains N-linked glycosylation sites which overlap with antigenic sites and are thought to be involved in the shielding of these antigenic sites from binding by antibodies and major histocompatibility complex (Skehel et al., 1984; Jackson et al., 1994). In addition, structural complexity of N-glycans is positively correlated with HA-receptor binding specificity (Tsuchia et al., 2002). The number of N-linked glycosylation sites in the globular head region of HA has increased during the evolution of H1N1 and H3N2 human Influenza A virus (Suzuki. 2011). We have determined a relationship between the numbers of predicted glycosylation sites on the HA molecule of Influenza A and the level of agglomeration present.

The numbers of glycosylation sites were predicted by calculating probability scores using an algorithm available on the NetNGlyc 1.0 Server. To produce a probability score the HA protein sequence of the strain in question is entered into the algorithms submission panel and submitted for analysis. The software produces a table of predicted glycosylation sites within the entered sequence which are scored with 1-3 plus (+) symbols depending on the strength of probability. A predicted HA glycosylation site probability score (pGly score) is defined as the sum of the plus symbols for a given output sequence. We propose that H3N2 strains that have a pGly score of ≥16 require sonication of ≥90 Joules/mL and H1N1 strains that have a pGly score≥11 require sonication of ≥90 Joules/mL (wherein more than 50% of the material is not aggregated).

TABLE 3 relationship between the numbers of predicted glycosylation sites on the HA1 molecule of Influenza A and the level of agglomeration present.

| STRAIN | YEAR | % ODT | Predicted HA Glyc. Sites (Prob. Score.) |
|---|---|---|---|
| H3N2 | | | |
| A/Hiroshima/52/05 | 2005 | 62 | 14 |
| A/Wisconsin/67/05 | 2005 | 86 | 16 |
| A/Brisbane/10/07 | 2007 | 44 | 17 |
| A/Uruguay/716/07 | 2007 | 65 | 16 |
| A/Wisconsin/15/09 | 2009 | 55.4 | 16 |
| A/Victoria/210/09 | 2009 | 42.8 | 17 |
| A/Victoria/361/11 | 2011 | 41.7 | 18 |
| A/Texas/50/12 | 2012 | 33.3 | 18 |
| A/South Australia/55/14 | 2014 | 33.6 | 17 |
| A/New Caledonia/71/14 | 2014 | 28.5 | 17 |
| A/Hong Kong/4801/14 | 2014 | 32.0 | 19 |
| A/Singapore/INFIMH-16-0019/2016 | 2016 | 18.0 | 19 |
| H1N1 | | | |
| A/California/07/09 | 2009 | 52.3 | 11 |
| A/Singapore/GP1908/15 | 2015 | 24.7 | 12 |

Alternative Physical Methods of Disruption to Disperse IVV Drug Substance

To assess the unique ability of sonication to disperse IVV Drug Matrix, other methods of physical disruption was examined. This included localized heat (microwave for 1 and 10 s) and shear force (dounce homogenization using 25 and 100 strokes). In either case there was no notable difference in dispersion compared to untreated material (Table 4).

TABLE 4

ODT results for A/Victoria/361/2011 IVV drug substance after microwave heating and shear force Dounce homogenization.

| | %ODT | Std dev (±) |
|---|---|---|
| A/Victoria/361/2011 IVV drug substance; untreated (control) | 38.1 | 0.1 |
| Microwave heating | | |
| 1 second | 37.2 | 0.3 |
| 10 seconds | 39.0 | 0.5 |

TABLE 4-continued

ODT results for A/Victoria/361/2011 IVV drug substance after microwave heating and shear force Dounce homogenization.

|  | %ODT | Std dev (±) |
|---|---|---|
| Dounce homogenization | | |
| 25 strokes | 40.5 | 1.5 |
| 100 strokes | 39.6 | 0.3 |

CONCLUSIONS

The use of a direct sonication method has been found to effectively disperse agglomerates within IVV Drug Matrix. Influenza strains within the sub-type: H3N2 exhibit the highest levels of agglomeration. Optimization of the process indicated that the amount of energy transferred to IVV Drug Matrix and the rate at which transfer occurred was essential in controlling the level of agglomerate dispersion. Increasing the rate of sonication (amplitude) and/or exposure time (seconds) resulted in an increase in the level of agglomerate dissociation which correlated with a linear trend. A plateau in the level of dispersion is observed after when the ODT reached 97% after which little or no more agglomerates were dispersed (as measured by ODT). The use of sonication as a method for dispersing agglomerates in IVV drug substance was evaluated over a time course of 24 weeks (6 months), both in the presence and absence of a detergent (PS80). Several characterization analytics including: ODT, DLS and EM revealed that the sonicated IVV Drug Matrix contained a significantly increased amount of dispersed material compared with the untreated and detergent-treated samples. The amount of sonication required to reach a target level of agglomerate dispersion could be predicted and was consistent between batches. Further, the level of dispersion remained consistent over the entire duration of the feasibility study thus indicating a stable and permanently agglomerate dispersed state. Immunological assessment by SRID confirmed that neither sonication nor detergent treatment compromised the antigenicity of the IVV Drug Matrix.

This work has strongly exemplified the value of sonication as a simple, practical and effective approach to improve the quality attributes of influenza vaccines that contain highly agglomerated IVV Drug Matrix. In addition, this method has also been shown to be applicable to all seasonal strains of influenza. Following sonication treatment, increased levels of dispersed material was observed in IVV Drug Matrix of H3N2, H1N1 and two influenza B strains of the Yamagata and Victoria lineages, which was well maintained over a six month period.

As an alternative to the direct sonication method designed for laboratory scale investigations, a continuous flow sonication configuration was investigated for processing commercial volumes of IVV Drug Matrix. In brief, the Sonicator unit is powered by a high frequency generator combined with a convertor at 20 kHz; the connecting booster horn is encased by a flow-through processing vessel containing the sample that is constantly recirculated at a nominated flow rate.

Figure 10:
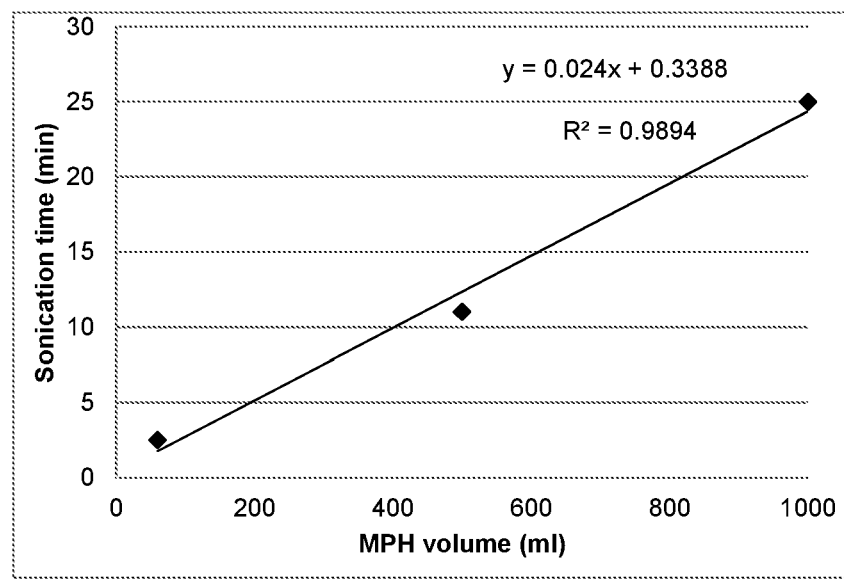
FIG. 10: Sonication exposure time (min) over IVV Drug Matrix batch volume (MPH volume mL) corresponding to ODT≥80%, for various IVV Drug Matrix batch volumes of 60, 500 and 1000 ml.
Figure 11:
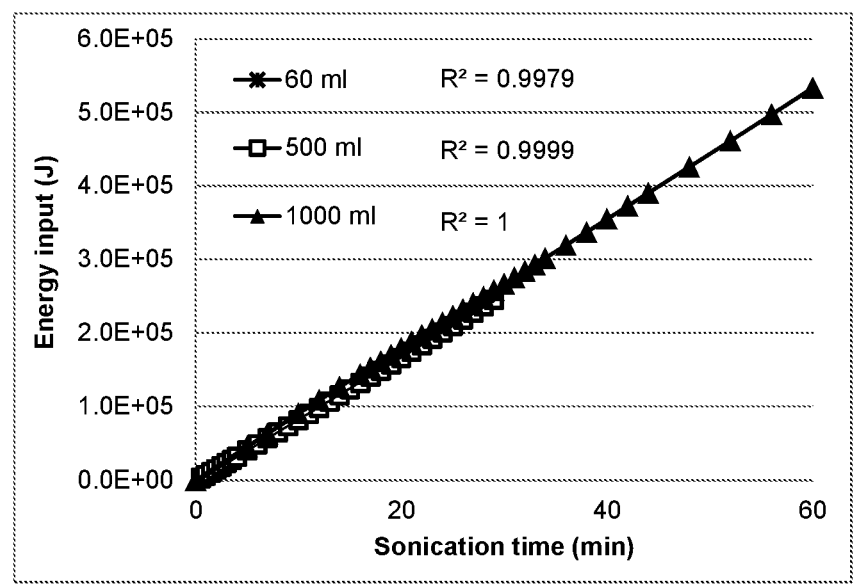
FIG. 11: Sonication energy input over processing time corresponding to ODT≥80%, for various IVV Drug Matrix batch volumes of 60, 500 and 1000 ml.
Figure 12:
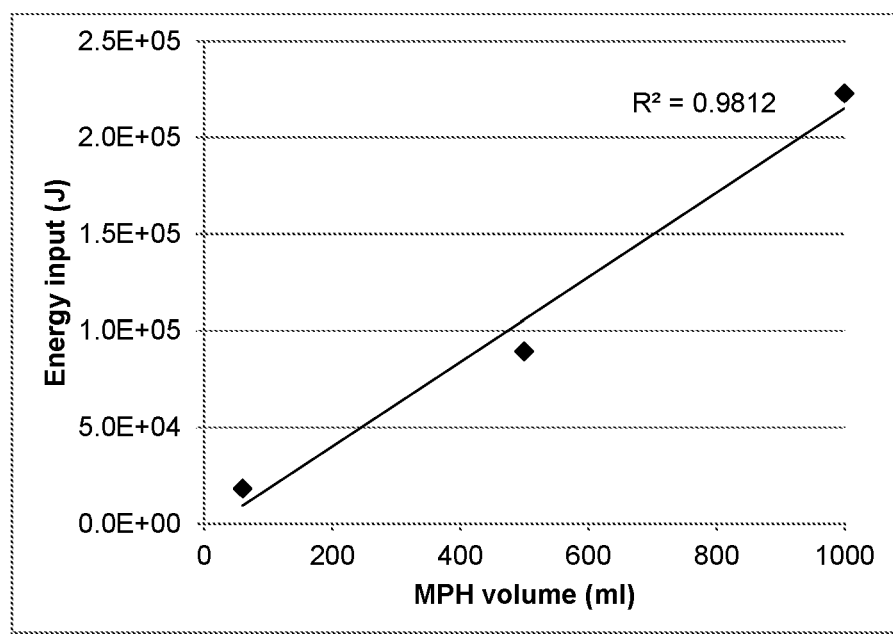
FIG. 12: Sonication energy input required to achieve ODT≥80%, using a flow-through device versus batch volume of IVV Drug Matrix (60, 500 and 1000 ml).

To evaluate the scalability of the system, the influence of various processing parameters, including: sonication intensity (amplitude) and product recirculation flow rate were investigated to determine the effect on the efficiency of agglomerate dispersion within IVV drug substance. Using a constant recirculation flow rate through the Sonicator of 120 ml/min and a fixed amplitude of 80%, a strong linear correlation was demonstrated between the batch volume (60, 500 and 1000 ml) and sonication time (over 60 minutes) required to reach an ODT threshold of 80% ($R^2=0.989$). This trend was also observed between sonication energy (Joules) and time ($R^2 \geq 0.998$), and hence between sonication energy and batch volume of IVV Drug Matrix ($R^2=0.981$, Table 5 and FIGS. 10-12). This data suggests the sonication process outlined is scalable with respect to IVV drug substance batch size. Further, the data suggests that a fixed energy input of at least 300 Joules/mL is sufficient to dissociate agglomerates to an ODT level of $\geq 80\%$, regardless of volume in this system.

TABLE 5

Sonication time and energy input required to achieve an ODT ≥80% during recirculation of IVV Drug Matrix in the flow through Sonicator for various batch volumes (80% amplitude; 120 ml/min IVV Drug Matrix flow rate).

| IVV Drug Matrix (ml) | Sonication time (sec) | Energy input (Joules) | Energy per mL (Joules/mL) | ODT (%) |
|---|---|---|---|---|
| 60 | 150 | 18272 | 305 | 83 |
| 500 | 660 | 89354 | 179 | 82 |
| 1000 | 1500 | 222953 | 223 | 83 |

Figure 13:
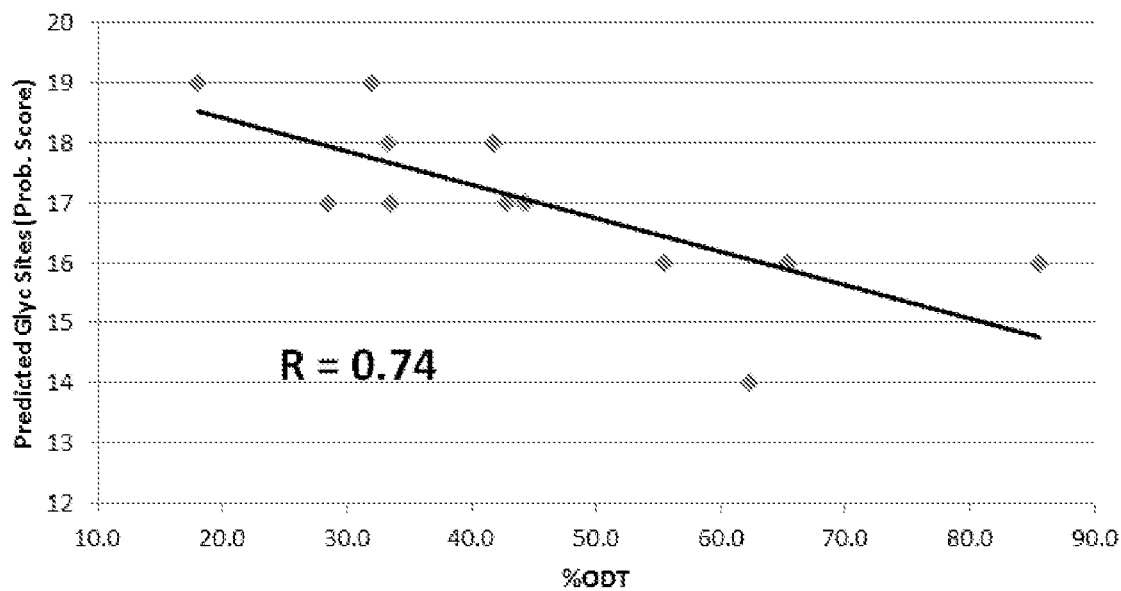
FIG. 13: Linear relationship between the amount of agglomeration in IVV Drug Matrix (depicted as % ODT) and the predicted number of glycosylation sites present on the HA molecule.

We have determined a linear relationship between the number of predicted glycosylation sites on the Influenza A HA molecule and the degree of agglomeration found in the IVV Drug Matrix of that strain (FIG. 13). A correlation co-efficient value (r value) was calculated for the relationship between predicted glycosylation sites and the degree of agglomeration for IVV Drug Matrix of 12 H3N2 strains manufactured between 2005 and 2017. The r value was 0.74 which suggests a moderately strong correlation for these two attributes. We propose that H3N2 strains that have a pGly score of ≥16 require sonication of ≥90 Joules/mL and H1N1 strains that have a pGly score≥11 require sonication of ≥90 Joules/mL

REFERENCES

[1] CDC. Seasonal Influenza Vaccine Safety: A Summary for Clinicians. 2011

[2] Fuminger IGS. Vaccine production. In: Nicholson K G, Webster R G, Hay A J, editors. Textbook of influenza Oxford: Blackwell Science, 1998: 324-32.

Smith T L, Jennings R., Specificity and in vitro transfer of the immunosuppressive effect of detergent-disrupted influenza virus vaccine, Clin Exp Immunol. 1990 January; 79(1):87-94.

Williams M S, Mayner R E, Daniel N J, Phelan M A, Rastogi S C, Bozeman F M, et al. New developments in the measurement of the hemagglutinin content of influenza virus vaccines by single-radial-immunodiffusion. J Biol Stand. 1980; 8(4):289-96 van de Donk H J, de Jong J C, van Olderen M F, Osterhaus A D. Monoclonal antibodies for the control of influenza virus vaccines. Developments in biological standardization. 1984; 57:251-5

Bhatti A, Siddiqui, Y M., Micusan, V V. Highly sensitive fluorogenic enzyme-linked immunosorbant assay: detection of staphylococcal enterotoxin B 1. Journal of Microbiological methods. 1994; 19:179-87

Skehel, J. J., Stevens, D. J., Daniels, R. S., Douglas, A. R., Knossow, M., Wilson, I. A., and Wiley, D. C. (1984) A carbohydrate sidechain on hemagglutinins of Hong Kong influenza viruses inhibits recognition by a monoclonal antibody. Annu. Rev. Biochem. 69, 531-569.

Jackson, D. C., Drummer, H. E., Urge, L., Otvos, L. Jr., and Brown, L. E. (1994) Glycosylation of a synthetic peptide representing a T cell determinant of influenza virus hemagglutinin results in loss of recognition by CD4+ T-cell clones. Virology 199, 422-430.

Tsuchiya, E., Sugawara, K., Hongo, S., Matsuzaki, Y., Muraki, Y., Li, Z.-N., and Nakamura, K. (2002) Effect of addition of new oligosaccharide chains to the globular head of influenza A/H2N2 virus hemagglutinin on the intracellular transport and biological activities of the molecule. J. Gen. Virol. 83, 1137-1146.

Suzuki, Y. (2011) Positive selection for gains of N-linked glycosylation sites in hemagglutinin during evolution of H3N2 human influenza A virus. Genes Genet. Syst. 86, 287-294.

The invention claimed is:

1. A method of dispersing agglomerated material in a preparation comprising influenza virus proteins, the method comprising subjecting the preparation to sonication; wherein the sonication is conducted at a rate of 80% amplitude.

2. The method according to claim 1, wherein the preparation comprises influenza virus haemagluttinin.

3. The method according to claim 1, wherein the preparation comprises split influenza virus virions.

4. The method according to claim 3, wherein the preparation comprises a level of less than 0.02% of detergent.

5. The method according to claim 1, wherein the sonication is conducted for a time and at intensity to disperse at least 50% of agglomerates present in the preparation.

6. The method according to claim 1, wherein the sonication is conducted to transfer at least 90 Joules/mL of energy.

7. The method according to claim 1, wherein influenza virus H3N2 strains that have a predicted HA glycosylation site probability score (pGly score) ≥16 require sonication of ≥90 Joules/mL and influenza virus H1N1 strains that have a pGly score ≥11 require sonication of ≥90 Joules/mL.

8. A method of producing an influenza virus vaccine, the method comprising producing a preparation comprising inactivated or split influenza virions and sonicating the preparation; wherein the sonication is conducted at a rate of 80% amplitude.

9. The method according to claim 8, wherein the vaccine comprises at least 3 different influenza virus strains.

10. The method according to claim 8, wherein the vaccine is a monovalent vaccine or a quadrivalent vaccine.

11. The method according to claim 8, wherein the vaccine comprises influenza virus A and influenza virus B.

12. The method according to claim 8, wherein the vaccine is substantially free of agglomerated material.

13. A method of dispersing agglomerated material in a preparation comprising influenza virus proteins, the method comprising subjecting the preparation to sonication; wherein the sonication is conducted to transfer at least 90 Joules/mL of energy.

14. A method of dispersing agglomerated material in a preparation comprising influenza virus proteins, the method comprising subjecting the preparation to sonication; wherein influenza virus H3N2 strains that have a predicted HA glycosylation site probability score (pGly score) ≥16 require sonication of ≥90 Joules/mL and H1N1 strains that have a pGly score ≥11 require sonication of ≥90 Joules/mL.

15. The method according to claim 13, wherein the preparation comprises inactivated or split influenza virus virions from at least 3 different influenza virus strains.

16. The method according to claim 13, wherein the preparation is a monovalent vaccine or a quadrivalent vaccine.

17. The method according to claim 13, wherein the preparation comprises influenza virus A and influenza virus B.

18. The method according to claim 14, wherein the preparation comprises inactivated or split influenza virus virions from at least 3 different influenza virus strains.

19. The method according to claim 14, wherein the preparation is a monovalent vaccine or a quadrivalent vaccine.

20. The method according to claim 14, wherein the preparation comprises influenza virus A and influenza virus B.

* * * * *